US005466603A

United States Patent [19]

Meehan et al.

[11] Patent Number: 5,466,603

[45] Date of Patent: Nov. 14, 1995

[54] TEMPERATURE REGULATED HYBRIDIZATION CHAMBER

[76] Inventors: Brian W. Meehan, 616 Wildwood, East Lansing, Mich. 48823; Uwe Heine, Department of HLA/Paternity Roche Biomedical Laboratories, Inc. 1447 York Ct., Burlington, N.C. 27215; James M. Mason, 50 Driftwood Ct., Gibsonville, N.C. 27249

[21] Appl. No.: 196,626

[22] Filed: Feb. 15, 1994

[51] Int. Cl.$^{6}$ .............................. C12M 1/38; C12M 1/02

[52] U.S. Cl. ...................................... 435/285.1; 435/286.1

[58] Field of Search .................................... 435/290, 316, 435/809; 422/102, 104; 165/109.1; 126/378; 354/299; 118/429, 407

[56] References Cited

U.S. PATENT DOCUMENTS

| | | | |
|---|---|---|---|
| 2,238,661 | 4/1941 | Shaeffer | 95/95 |
| 2,427,146 | 9/1947 | Lee | 126/378 |
| 3,013,548 | 12/1961 | Thomas | 126/378 |
| 3,332,338 | 7/1967 | Wein | 126/378 |
| 3,432,642 | 3/1969 | Lohr et al. | 126/378 |
| 3,438,317 | 4/1969 | Merolli et al. | 354/299 |
| 3,746,205 | 7/1973 | Helguera | 220/13 |
| 3,890,629 | 6/1975 | Huss | 354/299 |
| 3,986,934 | 10/1976 | Müller | 195/142 |
| 4,195,131 | 3/1980 | Papas | 435/291 |
| 4,301,252 | 11/1981 | Baker et al. | 435/290 |
| 4,906,578 | 3/1990 | Suzuki et al. | 135/316 |
| 5,012,763 | 5/1991 | Morrison | 119/34 |
| 5,061,448 | 10/1991 | Mahe et al. | 422/99 |
| 5,081,036 | 1/1992 | Familletti | 435/286 |
| 5,133,940 | 7/1992 | Kalkkinen et al. | 422/138 |
| 5,209,284 | 5/1993 | Okamoto et al. | 126/378 |
| 5,215,144 | 6/1993 | May et al. | 165/154 |

FOREIGN PATENT DOCUMENTS

| | | | |
|---|---|---|---|
| 0222432 | 5/1910 | Germany | 354/299 |

*Primary Examiner*—William H. Beisner
*Attorney, Agent, or Firm*—Panitch, Schwarze, Jacobs & Nadel

[57] ABSTRACT

A temperature regulated hybridization chamber which includes an outer container which defines a first chamber for receiving a first fluid having a predetermined temperature. The hybridization chamber includes an inner container having a generally horizontal bottom wall with a periphery and an inner container side wall extending generally upwardly from the periphery of the inner container bottom wall. The inner container bottom wall and the inner container side wall define a second chamber for receiving a second fluid. The inner container is positioned within the first chamber with the inner container bottom wall and the inner container side wall being spaced from the outer container bottom wall and the outer container side wall, respectively, such that when the first fluid is positioned within the first chamber the first fluid is in engagement with the inner container bottom wall and inner container side wall. A drain conduit is in fluid communication with the second chamber for removing the second fluid from the second chamber. The drain conduit is positioned such that the second fluid flows through the drain conduit due to the force of gravity such that the second fluid in the inner chamber is maintained at a temperature which is about equal to the predetermined temperature of the first fluid.

16 Claims, 1 Drawing Sheet

TEMPERATURE REGULATED HYBRIDIZATION CHAMBER

FIELD OF THE INVENTION

The present invention relates to a temperature regulated hybridization chamber and, more particularly, to a temperature regulated hybridization chamber which eliminates the handling of DNA membranes during the hybridization process and allows fluids to be transferred without significantly affecting chamber temperature.

BACKGROUND OF THE INVENTION

DNA membrane hybridizations occur at a fixed and very critical temperature. During the DNA membrane hybridization process it is often required that many solutions be removed from the hybridization chamber and replaced with other solutions. Conventional hybridization chambers do not allow for easily removing the solution from the hybridization chamber when it is necessary to replace the solution. Such conventional hybridization chambers often require that the chamber be removed from the heat source, drained and then returned to the heat source. This process often requires that the chamber be turned upside down or on its side and sometimes requires that the DNA membrane be removed from the chamber.

Hence, conventional hybridization chambers often result in significant temperature differences within the chamber during the hybridization process. Significant temperature differences within the hybridization chamber during the hybridization process can be problematic. For instance, in chemiluminescence DNA membrane hybridizations an enzyme is employed that cannot tolerate temperature fluctuations. Accordingly, significant temperature fluctuations can impair the hybridization process. A need has arisen for a hybridization chamber which eliminates the handling of the DNA membranes during the hybridization process and allows fluids within the chamber to be removed and replaced without affecting chamber temperature.

The present invention is directed to a temperature regulated hybridization chamber which allows DNA membranes in the chamber to be completely submerged under the solution within the chamber. The present invention also provides a bottom, gravity-fed drain for removing solution from the chamber to eliminate the handling of the DNA membranes. A removable cover member is positioned over the chamber to prevent the solution from evaporating from the chamber and to help maintain the temperature of the solution at the desired temperature during the hybridization process. Accordingly, use of the hybridization chamber of the present invention results in the DNA membranes being maintained at a constant temperature.

SUMMARY OF THE INVENTION

Briefly stated, the present invention is a temperature regulated hybridization chamber comprising an outer container including a bottom wall having a periphery and an outer container side wall extending generally upwardly from the periphery. The outer container bottom wall and the outer container side wall define a first chamber for receiving a first fluid having a predetermined temperature. The hybridization chamber further comprises an inner container including a bottom wall having a periphery and an inner container side wall extending generally upwardly from the periphery of the inner container bottom wall. The inner container bottom wall and the inner container side wall define a second chamber for receiving a second fluid. The inner container is positioned within the first chamber with the inner container bottom wall and inner container side wall being spaced from the outer container bottom wall and outer container side wall, respectively, such that when the first fluid is positioned within the first chamber the first fluid is in engagement with the inner container bottom wall and the inner container side wall. A drain conduit is in fluid communication with the second chamber for removing the second fluid from the second chamber. The drain conduit is positioned such that the second fluid flows through the drain conduit due to the force of gravity whereby the second fluid in the inner chamber is maintained at a temperature which is about equal to the predetermined temperature of the first fluid.

The present invention also provides for a removable cover member positioned over an opening defined by the inner container side wall for receiving the second fluid therethrough, to prevent the second fluid from evaporating through the opening and to help maintain the temperature of the second fluid at the predetermined temperature.

BRIEF DESCRIPTION OF THE DRAWING

The foregoing summary, as well as the following detailed description of the preferred embodiment of the invention, will be better understood when read in conjunction with the appended drawing. For the purpose of illustrating the invention, there is shown in the drawing an embodiment which is presently preferred. It should be understood, however, that the invention is not limited to the precise arrangements and instrumentalities shown. In the drawing.

DETAILED DESCRIPTION OF PREFERRED EMBODIMENT

Figure 2:
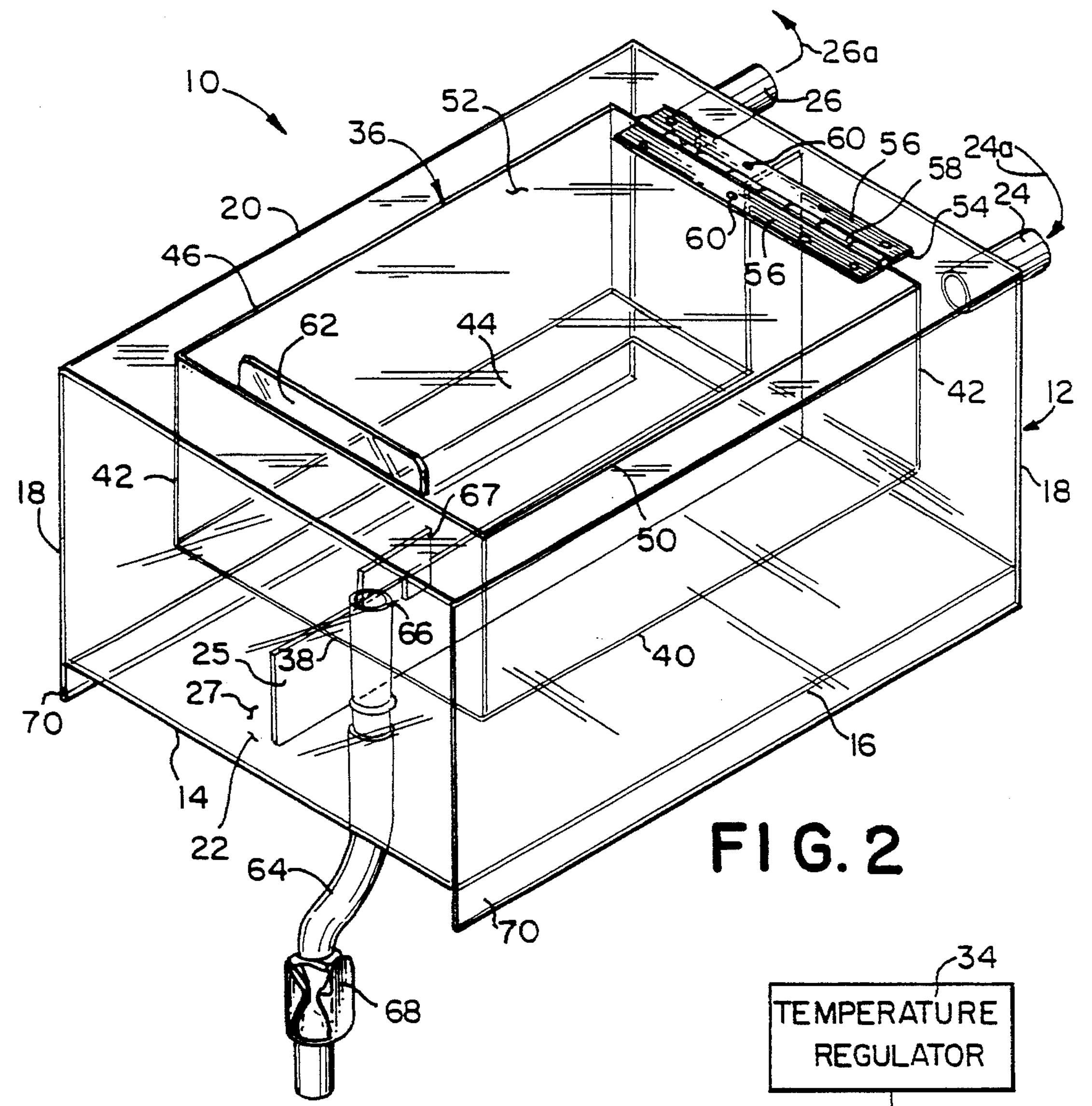
FIG. 2 is a perspective view of the hybridization chamber shown in FIG. 1.

Certain terminology is used in the following description for convenience only and is not limiting. The words "right," "left," "lower" and "upper" designate directions in the drawing to which reference is made. The words "inwardly" and "outwardly" refer to directions toward and away from, respectively, the geometric center of the temperature regulated hybridization chamber and designated parts thereof. The terminology includes the words above specifically mentioned, derivatives thereof and words of similar import.

Figure 1:
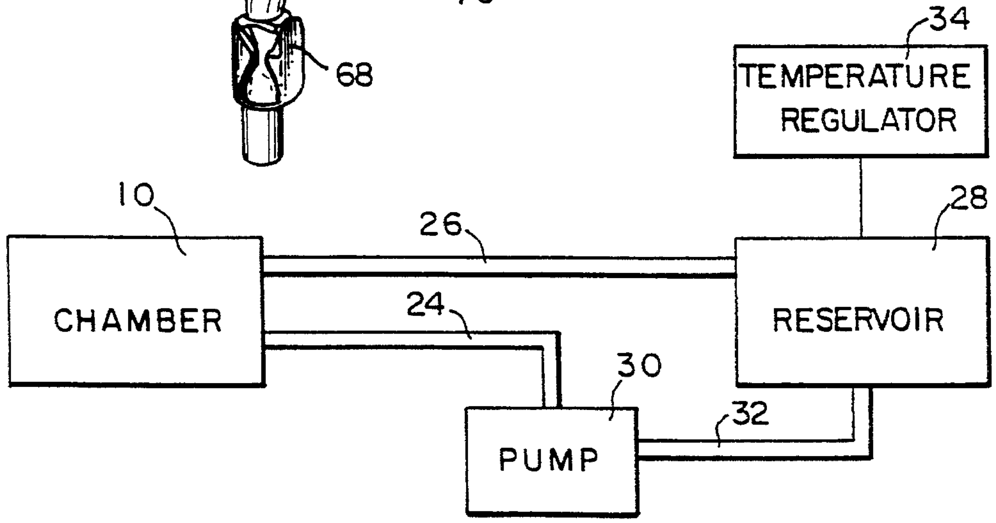
FIG. 1 is a schematic block diagram of a temperature regulated hybridization chamber in accordance with the present invention.

Referring now to the drawing in detail, wherein like numerals are used to indicate like elements throughout, there is shown in FIGS. 1 and 2 a temperature regulated hybridization chamber, generally designated 10, in accordance with the present invention. The hybridization chamber 10 is preferably used to hybridize DNA membranes. The hybridization of DNA membranes is a process well known to those of ordinary skill in the art and does not form a part of the present invention and, therefore, further description thereof is omitted for purposes of convenience only and is not limiting. While it is preferred that the hybridization chamber 10 be used to hybridize DNA membranes, it is understood by those skilled in the art form this disclosure that the hybridization chamber 10 could be used for other purposes, such as membrane stripping and incubations, without departing from the spirit and scope of the invention.

Referring now to FIG. 2, the hybridization chamber 10 includes an outer container 12 including a bottom wall 14 having a periphery 16, an outer container side wall 18 extending generally upwardly from the periphery 16 and a top wall 20 spaced from the bottom wall 14 such that the outer container side wall 18 extends between the top and bottom walls 14, 20. In the present embodiment, it is preferred that the top and bottom walls 14, 20 be generally planar and extend generally parallel with respect to each other and the outer container side wall 18 be generally in the form of a parallelogram in cross section such that the outer container 12 is generally in the form of a parallelepiped. While it is preferred that the outer container 12 be generally in the form of a parallelepiped, it is understood by those skilled in the art from this disclosure that the outer container 12 could be shaped in other manners without departing from the spirit and scope of the invention. For instance, the outer container side wall 18 could be configured generally in the form of a circle, oval, ellipse, triangle, or pentagon in cross section. Similarly, the bottom wall 14 and top wall 20 could be generally in the form of a semi-sphere or dome and the top wall 20 could be omitted.

In the present embodiment, it is preferred that the outer container 12 be constructed of generally rigid, high-strength, fluid impervious transparent material, such as acrylic. However, it is understood by those skilled in the art from this disclosure that the outer container 12 could be constructed of other materials, such as stainless steel, other polymers, brass or glass. It is preferred that the bottom wall 14, outer container side wall 18 and top wall 20 be sealingly secured together by an adhesive, although other methods could be used to assemble the outer container 12 depending upon the type of material used to construct the outer container 12. For instance, if the outer container 12 were constructed of stainless steel, a welding process would be used to assemble the outer container 12.

The outer container bottom wall 14 and the outer container side wall 18 define a first chamber 22 for receiving a first fluid (not shown) having a predetermined temperature. In the present embodiment, it is preferred that the first fluid have a relatively low viscosity to permit the first fluid to be readily pumped or circulated in and out of the first chamber 22, as described in more detail hereinafter. In the present embodiment, it is preferred that the first fluid be water, although other fluids, such as alcohol and coolants, could be used without departing from the spirit and scope of the invention. It is preferred that the predetermined temperature of the first fluid be in the range of about 40° to 60° C., since this is the optimum temperature range for hybridizing DNA membranes. However, it is understood by those skilled in the art from this disclosure that the present invention is not limited to any particular temperature of the first fluid, and that it may vary depending upon the process being carried out, without departing from the spirit and scope of the invention.

Referring now to FIGS. 1 and 2, the hybridization chamber 10 includes an inlet conduit 24 in fluid communication with the first chamber 22 for allowing the first fluid to flow into the first chamber 22 and an outlet conduit 26 in fluid communication with the first chamber 22 for removing the first fluid from the first chamber 22. The first chamber 22 is divided into two generally equal areas by a baffle plate 25 which sealingly extends between the inner container 36 and outer container 12, except for a relatively small flow through area 27 between the baffle 25 and the outer container side wall 18 at a point opposite from the location of the inlet and outlet conduits 24, 26, as described below. As best shown in FIG. 2, the inlet and outlet conduits 24, 26 are positioned near the top of the outer container side wall 18 and the arrows 24*a*, 26*a* indicate the direction of flow of the first fluid into and from the outer container 12. More particularly, the first fluid flows into the first chamber 22 through the inlet conduit 24 on one side of the baffle 25, through the flow through area 27 to the other side of the baffle 25 and out of the first chamber 22 through the outlet conduit 26. This insures that the first fluid flows completely around the inner container 36 to maintain a uniform temperature within the inner container 36.

Although it is understood by those skilled in the art from this disclosure that the inlet and outlet conduits 24, 26 could be positioned anywhere on the outer container 12 so long as an adequate amount of the first fluid is maintained within the first chamber 22, as described in more detail hereinafter. The inlet conduit 24 and outlet conduit 26 are preferably sealingly connected to the outer container side wall 18 in a manner well understood by those skilled in the art.

As shown in FIG. 1, the outlet conduit 26 is in fluid communication with a reservoir 28 which houses a sufficient supply of the first fluid to maintain the outer container 12 completely filled with the first fluid while continuously or periodically circulating the first fluid through the first chamber 22. The inlet conduit 24 is in fluid communication with a pump 30. A transfer conduit 32 fluidly couples the pump 30 to the reservoir 28. The outer container 12, inlet conduit 24, outlet conduit 26, reservoir 28, pump 30 and transfer conduit 32 preferably form a closed system. The temperature of the first fluid within the reservoir 28 is preferably controlled by a temperature regulator 34. The temperature regulator 34 controls the temperature of the first fluid within the reservoir 28 such that the temperature of the first fluid within the reservoir 28 is generally equal to the predetermined temperature.

The pump 30 preferably continuously circulates the first fluid from the reservoir 28 through the transfer conduit 32 and inlet conduit 24 into the first chamber 22 until the first chamber 22 is completely filled with the first fluid. Since the system is closed, the first fluid 22 flows from the first chamber 22 through the outlet conduit 26 into the reservoir 28. By continuously pumping the first fluid through the first chamber 22 and reservoir 28, the temperature of the first fluid is maintained at the predetermined temperature.

In the present embodiment, the temperature regulator 34, reservoir 28, transfer conduit 32 and pump 30 are an off-the-shelf system sold by Fisher Scientific of Pittsburgh, Pa. under the name Isotemp Constant Temperature Circulator, Model 801, although it is understood by those skilled in the art from this disclosure that other constant temperature circulators could be used without departing from the spirit and scope of the invention. While it is preferred that the temperature of the first fluid within the first chamber 22 be maintained by the system described above, it is understood by those skilled in the art from this disclosure that other methods and systems could be used for maintaining the temperature of the first fluid within the first chamber 22. For instance, the first fluid could not be circulated in and out of the first chamber 22 and, instead, externally controlled heating/cooling elements (not shown) could be provided within the first chamber 22 to maintain the temperature of the first fluid.

Referring now to FIG. 2, the hybridization chamber 10 further includes an inner container 36. The inner container 36 includes a generally horizontal bottom wall 38 having a periphery 40 and an inner container side wall 42 extending generally upwardly from the periphery 40 of the inner container bottom wall 38. The inner container bottom wall 38 and the inner container side wall 42 define a second chamber 44 for receiving a second fluid (not shown). The inner container 36 is shaped generally in the same manner as the outer container 12, except that the inner container 36 is smaller to permit the inner container 36 to be positioned within the first chamber 22 with the inner container bottom wall 38 and inner container side wall 42 being spaced from the outer container bottom wall 14 and the outer container side wall 18, respectively, such that when the first fluid is positioned within the first chamber 22 the first fluid is in engagement with the inner container bottom wall 38 and the inner container side wall 42.

More particularly, the top wall 20 includes an opening 46 which is complementarily sized to receive the inner container 36 therethrough. In the present embodiment, it is preferred that the inner container 36 be supported by and suspended from the top wall 20 of the outer container 12. Preferably, the inner container side wall 42 is secured to the edge of the top wall 20 which defines the opening 46 in any conventional manner, such as by an adhesive. However, it is understood by those skilled in the art from this disclosure that the inner container side wall 42 could be sealingly secured to the top wall 20 in other manners, such as with standard fasteners and a sealant material.

While it is preferred that the inner container 36 be shaped to correspond to the configuration of the outer container 12, it is understood by those skilled in the art from this disclosure that the inner container 36 could be of other configurations. For instance, the inner container side wall 42 could be shaped generally in the form of a circle, triangle, oval, ellipse or pentagon, without departing from the spirit and scope of the invention, so long as the inner container bottom wall 38 and inner container side wall 42 are spaced from the outer container bottom wall 14 and outer container side wall 18, respectively.

In the present embodiment, it is preferred that the second fluid be selected in accordance with the particular hybridization process which is to be carried out in the hybridization chamber 10. For instance, in chemiluminescence DNA membrane hybridizations, it is preferred that the second fluid be a saline solution. However, it is understood by those skilled in the art from this disclosure that other second fluids could be utilized, such as buffers and biological solutions, depending upon the type of hybridization process being carried out.

In the present embodiment, it is preferred that the inner container 36 be constructed of a relatively rigid, lightweight, high strength transparent material, which is preferably inert with respect to the second fluid, such as acrylic. However, it is understood by those skilled in the art from this disclosure that the inner container 36 could be constructed of other materials, such as stainless steel, other polymers, brass or glass, without departing from the spirit and scope of the invention.

In the present embodiment, it is preferred that the inner container 36 be located within the first chamber 22 such that when the first fluid is positioned within the first chamber 22, the first fluid is in sufficient facing engagement with the inner container bottom wall 38 and the inner container side wall 42 to cause the second fluid to have a temperature which is substantially equal to the predetermined temperature of the first fluid. That is, as best shown in FIG. 2, it is preferred that the inner container 36 be positioned within the first chamber 22 such that the first fluid completely envelops the inner container bottom wall 38 and all four planar surfaces of the inner container side wall 42 to achieve the best possible heat transfer and control of the temperature of the second fluid within the inner container 36. However, it is understood by those skilled in the art from this disclosure that the first fluid need not necessarily completely envelop the inner container bottom wall 38 and inner container side wall 42, so long as the temperature of the second fluid is substantially equal to the predetermined temperature of the first fluid.

Referring now to FIG. 2, the inner container side wall 42 defines an opening 50 for receiving the second fluid therethrough. The opening 50 generally corresponds to the opening 46 in the top wall 20. A removable, generally planar cover member 52 is positioned over the opening 50 in the inner container 36 to prevent the second fluid from evaporating through the opening 50 and to help maintain the temperature of the second fluid at the predetermined temperature. The cover member 52 is preferably sized to complement the opening 50 of the inner container 36 and is constructed of the same material as the inner container 36.

A hinge 54 is interconnected between the top wall 20 of the container 12 and the cover member 52 for allowing the cover member 52 to move between a first position (shown in FIG. 2) wherein the cover member 52 is positioned over and closing the opening 50 to prevent the second fluid from evaporating through the opening 50 and to help maintain the temperature of the second fluid at the predetermined temperature, and a second position (not shown) wherein the cover member 52 is positioned away from the opening 50 to allow the second fluid to be inserted into the inner container 36 through the opening 50. The hinge 54 is a standard pin hinge having a pair of leaves 56, a knuckle 58 and a pin (not shown) extending through the knuckle 58, wherein the leaves 56 are secured to the cover member 52 and top wall 20 using standard fasteners, such as screws 60, in a manner well understood by those skilled in the art.

While it is preferred that the cover member 52 be hingedly secured to the top wall 20 of the outer container 12, it is understood by those skilled in the art from this disclosure that the cover member 52 could be positioned for closing the opening 50 in other manners. For instance, the cover member 52 could merely rest within the opening 50 on the upper edges of the inner container side wall 42 or could take the form of a sliding horizontal door. As shown in FIG. 2, a handle 62 is provided for assisting in removing the cover member 52 from the outer container 12.

As shown in FIG. 2, a drain conduit 64 is in fluid communication with the second chamber 44 for removing the second fluid from the second chamber 44. The drain conduit 64 is positioned such that the second fluid flows through the drain conduit 64 due to the force of gravity. More particularly, one end of the drain conduit 64 sealingly extends from an opening 66 in the inner container bottom wall 38 through the first chamber 22 and outer container bottom wall 14. A generally L-shaped block 67 is positioned over opening 66 to prevent DNA membranes from covering the opening 66. As best shown in FIG. 2, the drain conduit 64 extends generally vertically from the inner container bottom wall 38 such that the second fluid flows from the second chamber 44 through the drain conduit 64 due to the force of gravity. The other end (not shown) of the drain conduit 64 is preferably in fluid communication with a container or waste removal system (not shown). The drain conduit 64 preferably sealingly extends through the outer container bottom wall 14 and is sealingly connected to the opening 66 in the inner container bottom wall 38 in a manner well understood by those skilled in the art. Accordingly, further description thereof is omitted for purposes of convenience only and is not limiting.

The drain conduit 64 is preferably constructed of a generally flexible polymeric material, such as polyethylene or polypropylene, and is generally circular in cross section. However, is it understood by those skilled in the art from this disclosure that the drain conduit 64 could be constructed of other materials, such as copper or an elastomeric material and configured in other shapes, such as generally square in cross section.

As shown in FIG. 2, the drain conduit 64 further includes a flow prevention device 68 located externally to the outer container 12 for selectively preventing the second fluid from flowing through the drain conduit 64. In the present embodiment, it is preferred that the flow prevention device 68 be a clamp of the type used in the medical field to pinch intravenous tubing. However, it is understood by those skilled in the art from this disclosure that other flow prevention devices could be used without departing from the spirit and scope of the invention, such as a ball valve or a solenoid actuated valve.

As shown in FIG. 2, a pair of legs 70 extend downwardly from the outer container side wall 18 for supporting the hybridization chamber 10 above a support surface (not shown) and for providing clearance for the drain conduit 64. It is preferred that the hybridization chamber 10 be supported on a device for agitating the hybridization chamber 10 in a manner well understood by those skilled in the art. It is preferred that the hybridization chamber 10 be agitated in an orbital path at a frequency of about one hundred orbits per minute. While it is preferred that the agitation be carried out in an orbitable path, it is understood by those skilled in the art from this disclosure that the hybridization chamber 10 could be agitated in any manner and at other frequencies, such as back-and-forth, without departing from the spirit and scope of the invention.

In use, the reservoir 28 is filled with the first fluid and the pump 30 and temperature regulator 34 are turned on to begin continuously circulating the first fluid through the first chamber 22. The temperature regulator 34 is preferably set to maintain the temperature of a first fluid at the predetermined temperature, for instance 50° C. to maintain the temperature within the first and second chambers 22, 44. Once the first fluid within the first chamber 22 has achieved the predetermined temperature and the inner container 36 has also achieved the predetermined temperature, the user grasps the handle 62 and lifts the cover member 52 to access the second chamber 44. The second fluid, preferably having a temperature a few degrees above the predetermined temperature of the first fluid, is then deposited or poured through the opening 50 of the inner container 36. This is to allow for the loss in temperature of the second fluid while it is poured into the second chamber 44.

After the second fluid is deposited into the second chamber 44, nylon membranes, having attached DNA, are positioned within the second chamber 44 until the nylon membranes are completely submerged within the second fluid. The agitator is then turned on and the hybridization process begins. Most hybridization processes require that the second fluid be changed on a regular basis, such as every five, ten or twenty minutes or a combination thereof. To change the second fluid, all that is necessary is to open the flow-prevention device 68 to drain the second fluid from the second chamber 44 through the drain conduit 64. After the second fluid has been drained from the second chamber 44, replacement second fluid is deposited into the second chamber 44 in the same manner as described above.

The process of changing the second fluid is then repeatedly carried out until the hybridization process is complete, at which point the nylon membranes can be removed and carried to a different station for further processing. Since the temperature of the second fluid is regulated and can be changed without handling the nylon membranes, the hybridization process is carried out without affecting the temperature within the second chamber.

While in the present embodiment, the temperature regulation of the first fluid and the draining and replacing of the second fluid in the second chamber is carried out generally manually, it is understood by those skilled in the art from this disclosure that a computer-controlled system could be utilized to maintain the temperature of the first fluid and to drain and replace the second fluid from the second chamber 44, without departing from the spirit and scope of the invention.

It will be appreciated by those skilled in the art from this disclosure that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A temperature regulated hybridization chamber for hybridization of DNA membranes comprising:

an outer container including a bottom wall having a periphery and an outer container side wall extending generally upwardly from said periphery, said outer container bottom wall and said outer container side wall defining a first chamber for receiving a first fluid having a predetermined temperature;

an inner container including a bottom wall having a periphery and an inner container side wall extending generally upwardly from said periphery of said inner container bottom wall, said inner container bottom wall and said inner container side wall defining a second chamber for receiving a second fluid and said DNA membranes, said inner container being positioned within said first chamber with said inner container bottom wall and inner container side wall being spaced from said outer container bottom wall and outer container side wall, respectively, such that when the first fluid is positioned within said first chamber the first fluid is in engagement with said inner container bottom wall and inner container side wall;

a drain conduit in fluid communication with said second chamber for removing the second fluid from said second chamber, said drain conduit being offset from a center of said bottom wall of said inner container and positioned such that the second fluid and not the DNA membranes flows through said drain conduit due to the force of gravity whereby the second fluid in said inner chamber is maintained at a temperature which is about equal to the predetermined temperature of the first fluid;

a block member positioned over at least a portion of said drain conduit also for preventing DNA membranes from flowing into said drain conduit;

an inlet conduit in fluid communication with said first chamber for allowing the first fluid to flow into said first chamber; and an outlet conduit in fluid communication with said first chamber for removing the first fluid from said first chamber.

2. The hybridization chamber as recited in claim 1 wherein said inner container is constructed of an inert material with respect to the second fluid.

3. The hybridization chamber as recited in claim 1 wherein said inner container side wall defines an opening for receiving the second fluid therethrough.

4. The hybridization chamber as recited in claim 3 further comprising a removable cover member positioned over said opening to prevent the second fluid from evaporating through said opening and to help maintain the temperature of the second fluid at the predetermined temperature.

5. The hybridization chamber as recited in claim 1 wherein said drain conduit sealingly extends from an opening in said inner container bottom wall through said first chamber and outer container bottom wall.

6. The hybridization chamber as recited in claim 1 wherein said drain conduit further includes a flow prevention device for selectively preventing the second fluid from flowing through said drain conduit.

7. The hybridization chamber as recited in claim 1 wherein said outer container side wall and said inner container side wall are generally in the form of a parallelogram in cross section.

8. The hybridization chamber as recited in claim 1 wherein the inner container bottom wall is generally horizontal.

9. A temperature regulated hybridization chamber for hybridization of DNA membranes comprising:

an outer container including a bottom wall having a periphery and an outer container side wall extending generally upwardly from said periphery, said outer container bottom wall and said outer container side wall defining a first chamber for receiving a first fluid having a predetermined temperature;

an inner container including a generally horizontal bottom wall having a periphery and an inner container side wall extending generally upwardly from said periphery of said inner container bottom wall, said inner container bottom wall and said inner container side wall defining a second chamber for receiving a second fluid and said DNA membranes, said inner container side wall defining an opening for receiving the second fluid and the DNA membranes therethrough, said inner container being positioned within said first chamber with said inner container bottom wall and inner container side wall being spaced from said outer container bottom wall and outer container side wall, respectively, such that when the first fluid is positioned within said first chamber the first fluid is in engagement with said inner container bottom wall and inner container side wall to maintain the second fluid in said inner chamber at a temperature which is about equal to the predetermined temperature of the first fluid;

a drain conduit in fluid communication with said second chamber for removing the second fluid from said second chamber, said drain conduit being offset from a center of said bottom wall of said inner container and positioned such that the second fluid and not the DNA membranes flows through said drain conduit due to the force of gravity whereby the second fluid in said inner chamber is maintained at a temperature which is about equal to the predetermined temperature of the first fluid;

a block member positioned over at least a portion of said drain conduit also for preventing DNA membranes from flowing into said drain conduit;

a removable cover member positioned over said opening to prevent the second fluid from evaporating through said opening and to help maintain the temperature of the second fluid at the predetermined temperature; and a hinge interconnected between said outer container and said cover member for allowing said cover member to move between a first position wherein said cover member is positioned over said opening to prevent the second fluid from evaporating through said opening and to help maintain the temperature of the second fluid at the predetermined temperature and a second position wherein said cover member is positioned away from said opening to allow the second fluid to be removed from said inner container through said opening.

10. The hybridization chamber as recited in claim 9 further comprising:

an inlet conduit in fluid communication with said first chamber for allowing the first fluid to flow into said first chamber; and an outlet conduit in fluid communication with said first chamber for removing the first fluid from said first chamber.

11. The hybridization chamber as recited in claim 9 wherein said inner container is constructed of an inert material with respect to the second fluid.

12. The hybridization chamber as recited in claim 9 wherein said outer container side wall and said inner container side wall are generally in the form of a parallelogram in cross section.

13. A temperature regulated hybridization chamber for hybridization of DNA membranes comprising:

an outer container including a bottom wall having a periphery and an outer container side wall extending generally upwardly from said periphery, said outer container bottom wall and said outer container side wall defining a first chamber for receiving a first fluid having a predetermined temperature;

an inner container including a bottom wall having a periphery and an inner container side wall extending generally upwardly from said periphery of said inner container bottom wall, said inner container bottom wall and said inner container side wall defining a second chamber for receiving a second fluid and said DNA membranes, said inner container being positioned within said first chamber with said inner container bottom wall and inner container side wall being spaced from said outer container bottom wall and outer container side wall, respectively, such that when the first fluid is positioned within said first chamber the first fluid is in engagement with said inner container bottom wall and inner container side wall, whereby the second fluid in said inner chamber is maintained at a temperature which is about equal to the predetermined temperature of the first fluid, and wherein said inner container side wall defines an opening for receiving the second fluid and said DNA membranes therethrough, said inner container being constructed of an inert material with respect to the second fluid;

an inlet conduit in fluid communication with said first chamber for allowing the first fluid to flow into said first chamber;

an outlet conduit in fluid communication with said first chamber for removing the first fluid from said first chamber;

a drain conduit in fluid communication with said second chamber for removing the second fluid from said second chamber, said drain conduit being positioned such that the second fluid flows through said drain conduit due to the force of gravity and such that said drain conduit is offset from a center of the second chamber for preventing DNA membranes from flowing into said drain conduit;

a generally L-shaped block member positioned over said drain conduit also for preventing DNA membranes from flowing into said drain conduit;

a removable cover member positioned over said opening to prevent the second fluid from evaporating through said opening and to help maintain the temperature of the second fluid at the predetermined temperature; and a hinge interconnected between said outer container and said cover member for allowing said cover member to move between a first position wherein said cover member is positioned over said opening to prevent the second fluid from evaporating through said opening and to help maintain the temperature of the second fluid at the predetermined temperature and a second position wherein said cover member is positioned away from said opening to allow the second fluid to be inserted into said inner container through said opening.

14. The hybridization chamber as recited in claim 13 wherein said inner container is constructed of an inert material with respect to the second fluid.

15. The hybridization chamber as recited in claim 13 wherein said inner container and said outer container are constructed from an optically clear material.

16. The hybridization chamber as recited in claim 13 wherein said outer container side wall and said inner container side wall are generally in the form of a parallelogram in cross-section and said inner container bottom wall is generally horizontal.

* * * * *